United States Patent [19]

Vanderpool et al.

[11] 4,337,369
[45] Jun. 29, 1982

[54] METHOD OF DECOLORIZING MIXTURES OF T-BUTYL ALKYLPHENOLS

[75] Inventors: Steven H. Vanderpool, Austin; Ernest L. Yeakey, Houston, both of Tex.

[73] Assignee: Texaco Inc., White Plains, N.Y.

[21] Appl. No.: 229,822

[22] Filed: Jan. 30, 1981

[51] Int. Cl.$^3$ .................. C07C 37/68; C07C 39/04
[52] U.S. Cl. ............................ 568/756; 568/749; 568/788; 568/793
[58] Field of Search ............. 568/756, 749, 788, 793, 568/750

[56] References Cited

U.S. PATENT DOCUMENTS

| | | | |
|---|---|---|---|
| 3,306,938 | 2/1967 | Welch et al. | 260/624 |
| 3,375,284 | 3/1968 | Zika et al. | 260/613 |
| 3,437,699 | 4/1969 | Flickinger | 260/621 |
| 3,454,654 | 7/1969 | Hobbs | 260/623 |
| 3,546,302 | 12/1970 | Asadorian et al. | 260/619 |
| 3,687,999 | 8/1972 | Kapur et al. | 260/458 |
| 4,101,590 | 7/1978 | Sato et al. | 568/756 |
| 4,138,591 | 2/1979 | Baur et al. | 568/756 |
| 4,202,199 | 5/1980 | Merger et al. | 568/788 |

FOREIGN PATENT DOCUMENTS

| | | |
|---|---|---|
| 1502518 | 11/1967 | France . |
| 1597867 | 8/1970 | France . |
| 46-02897 | 1/1971 | Japan . |
| 46-06869 | 2/1971 | Japan . |
| 49-31631 | 3/1974 | Japan . |
| 52-68134 | 6/1977 | Japan . |
| 6516378 | 6/1966 | Netherlands . |

OTHER PUBLICATIONS

Abram, J. C. et al., "Mechanism of color removal by ion exchange resins," Sucr. Belge/Sugar Ind. Abstr., vol. 90, No. 11, 1971, pp. 525-532.

Urban, M. et al., "Hydrazine Hydrate as Antioxidant Additive for Monohydric Phenols," Sb. Pr. Vyzk. Chem. Vyuziti Uhli, Dehtu Ropy, No. 10, 1970, pp. 65-78.

Primary Examiner—Werren B. Lone
Attorney, Agent, or Firm—Carl G. Ries; Jack H. Park; David L. Mossman

[57] ABSTRACT

A method of eliminating color-causing impurities in mixtures of t-butylalkyl phenols by treatment with trioxane at 100° C. and 1 atmospheric pressure is described. These phenols are used as peroxide inhibitors in polyol formulations for polyurethane foams. Discoloration of the polyol occurs if the phenol mixture is not treated with trioxane. It is an essential part of the invention that the t-butyl alkylphenol mixture be derived from an alkylphenol made over an acid resin catalyst. Mixtures made by a BF$_3$ process may not be decolorized by this method. Generally, the color decreases with increasing amounts of trioxane.

11 Claims, No Drawings

METHOD OF DECOLORIZING MIXTURES OF T-BUTYL ALKYLPHENOLS

BACKGROUND OF THE INVENTION

1. Field of the Invention

The invention relates to methods for treating mixtures of alkyl substituted phenols so that they will not cause discoloration when used as peroxide inhibitors in polyols and more particularly relates to methods of treating mixtures of alkyl substituted phenols by means of the addition of trioxane.

2. Prior Art

Many decolorizing agents now in use remove color by physical adsorption. The most common materials to remove color by this means are represented by charcoals, blacks (such as carbon black), clays and earths. Other compounds remove color by chemical reaction and are frequently more specific as to the materials they can remove color from than the physical adsorption agents. While attempts have been made to predict compound colors, such as by electronegative or steric contributions of substituents to aromatic rings, numerous exceptions to rules relating color to structure require color prediction to be based largely on empirical observations.* As a result, attempts to remove color from a specific compound tend to be strictly trial and error operations. *Griffiths, John. *Colour and Constitution of Organic Molecules.* London: Academic Press (1976), pp. 89–90.

With regard to the instant invention, a problem arose in finding a substitute for 2,6-di-t-butyl-paracresol which is used as a peroxide inhibitor in commercial polyol formulations. As the supplies of the paracresol became short, other compounds were tried as inhibitors. It was found that di-t-butyl nonylphenol would give the desired peroxide inhibiting effect and would help prevent scorching of the resultant foam made from the polyol formulation. However, it was discovered that this inhibitor would cause undesirable discoloration of the polyol and the subsequent foam. It is therefore an object of this invention to find an agent which will remove the color from the nonylphenol inhibitor.

SUMMARY OF THE INVENTION

The invention concerns a method for decolorizing a mixture of alkyl substituted phenols derived from a mono alkylphenol made over an anionic ion-exchange resin catalyst comprising reacting the mixture with a portion of trioxane.

DETAILED DESCRIPTION OF THE PREFERRED EMBODIMENTS OF THE INVENTION

The nonylphenol found to be useful as a precursor to a peroxide inhibitor in polyol formulations may be produced by at least two routes. One route uses an anionic ion-exchange resin catalyst such as a sulfonic acid resin to react propylene trimer while the other employs $BF_3$ as a catalyst. The nonylphenol is then reacted with a three-fold excess of isobutylene to obtain a mixture of butyl substituted phenols. The composition of the mixture used in the examples presented herein is mostly di-t-butyl nonylphenol, with some mono-5-butyl nonylphenol and nonylphenol.

It is suspected that the color of the di-t-butyl nonylphenol mixture is due to small amounts of compounds that have one substitution and one vacancy for the ortho positions on the phenyl ring adjacent to the hydroxyl group. Such a compound may be represented by the following structure

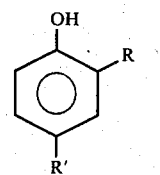

where R and R' are the same or different alkyl groups. For the particular mixture of the examples herein, it is expected that the compound causing the color has R equal to a tert-butyl group and R' equal to nonylalkyl.

The decolorizing agent of this invention is trioxane, the cyclic trimer of formaldehyde. It is theorized that trioxane removes the color by decomposing into formaldehyde moieties which react with the carbon in position 5 on the phenyl ring shown above. Theoretically, one trioxane molecule could bind up a maximum of six suspected color-causing molecules and convert them into compounds which do not contribute color to the mixture. This proposed mechanism has not been confirmed at this point. As formaldehyde is expected to be the active agent in this inventive process, it is anticipated that formaldehyde itself, dioxane and perhaps higher polymers of formaldehyde would be useful in the method of this invention. A pressurized system must be used if formaldehyde is to be employed as the decolorizer due to its high volatility.

Because trioxane boils at 115° C. under standard conditions, the decolorization reaction should be carried out at a temperature below this point. It is especially preferred that the reaction be conducted at temperatures between 25° to 100° C. It is also preferred that the reaction be performed at a pressure ranging from ambient to about 100 psig. As atmospheric pressure is easiest to work with, it is especially preferred. Generally, the conditions should be those necessary to keep all components in solution in light of the fact that solid trioxane sublimes at 45° to 50° C.

In the examples of this invention, nonylphenol made using a sulfonic acid resin or the $BF_3$ process was reacted with a three-fold excess of isobutylene to obtain a mixture of approximately 95 wt.% di-t-butyl nonylphenol, 4.5% mono-5-butyl nonylphenol and 0.5% nonylphenol, on a lights-free basis. This inhibitor mixture was then added to THANOL ® F-3016 polyol, which is made by Texaco Chemical Company and which has a hydroxyl number of 56, in a concentration of 4,000 ppm, inhibitor to polyol. Vanlube ® 81 octylated diphenyl amine made by R. T. Vanderbilt Company is added to a concentration of 600 ppm. The di-t-butyl nonylphenol and the amine combine to form a synergistic effect that raises the decomposition point of the polyol more than either component alone.

Each mixed alkylphenol sample was either not treated, or treated by recycle or with trioxane or both. The degree of color of the polyol after the treated phenol mixture is added is reported in Table I along with the resulting decomposition points of the polyol compositions.

TABLE I

| Example Number | Treatment | Nonyl-phenol | Decomp. Pt., °C. | Color Pt—Co[c] |
|---|---|---|---|---|
| 1 | None | [a] | 194 | 75 |
| 2 | Recycle | [a] | 190 | 100-125 |
| 3 | 3.3% Trioxane | [a] | 193 | 75 |
| 4 | 10% Trioxane | [a] | 193 | 40 |
| 5 | Recycle + 16% Trioxane | [a] | 188 | 30 |
| 6 | None | [b] | 196 | 75-100 |
| 7 | 3% Trioxane | [b] | 196 | 125 |
| 8 | 10% Trioxane | [b] | 192 | 125-150 |
| 9 | 16% Trioxane | [b] | 196 | 100-125 |

[a]Nonylphenol was made over a sulfonic acid resin.
[b]Nonylphenol was made with BF$_3$ process.
[c]Measure of color of polyol, color increases with increasing number.

The untreated polyol compositions had Pt-Co numbers in the range of 75 to 100. If the mixed alkylphenol is recycled over the sulfonic acid resin again with a three-fold excess of isobutylene as in Example 2, it becomes more colored, having a Pt-Co number between 100 and 125. In Examples 3, 4 and 5, a sample of phenol mix from Example 1 or 2 was reacted overnight at 100° C. with the indicated amount of trioxane. It may be seen that the color of the subsequent polyol decreased with increasing amounts of trioxane. However, in Examples 7, 8 and 9 where the mixed alkylphenols from the BF$_3$-made nonylphenol were reacted overnight at 100° C., no advantage in the color of the prepared polyol was found. It may be concluded that the method of invention works well only if the nonylphenol precursor is made over an anionic ion-exchange resin catalyst. If the nonylphenol is made using a BF$_3$ catalyst, the method of this invention will not decolorize the resulting mixture of alkylphenols. It is suspected that the color-causing impurities from the latter method are different from those from the acid resin method. It is further expected that the method of this invention would work on any di-substituted phenol with an alkyl substituent in the para- and one of the ortho positions. One skilled in the art will be able to modify and refine the method of this invention, the scope of which is limited only by the appended claims.

We claim:

1. A method for decolorizing a mixture of t-butyl alkylphenols derived by reacting a mono alkylphenol with isobutylene where the mono alkylphenol is made over an anionic ion-exchange resin catalyst comprising reacting the mixture with a portion of trioxane in a homogeneous liquid phase reaction.

2. The method of claim 1 where the mixture to be decolorized contains compounds of the formula

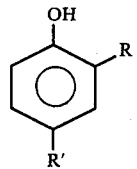

where R is a t-butyl group and R' is an alkyl group.

3. The method of claim 1 in which the amount of trioxane used is 1 to 20 weight percent of the mixture to be decolorized.

4. The method of claim 1 in which the mono alkylphenol is nonylphenol.

5. The method of claims 1, 2, 3 or 4 in which the decolorization reaction takes place at a temperature in the range of 25° to 115° C. and a pressure in the range of atmospheric to 100 psig.

6. A method for decolorizing a mixture of t-butyl alkylphenols containing compounds of the formula

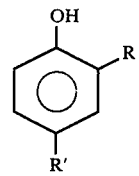

where R is a t-butyl group and R' is an alkyl group derived by reacting a mono alkylphenol with isobutylene where the mono alkylphenol is made over an anionic ion-exchange resin catalyst comprising reacting the mixture with trioxane in proportions of 1 to 20 weight percent of the mixture in a homogeneous liquid phase reaction at a temperature in the range of 25° to 115° C. and a pressure in the range of atmospheric to 100 psig.

7. A method for decolorizing a mixture of t-butyl nonylphenols derived by reacting isobutylene with nonylphenol where the nonylphenol is made over an anionic ion-exchange resin catalyst comprising reacting the mixture with 1 to 20 weight percent of trioxane in a homogeneous liquid phase reaction.

8. The method of claim 7 in which the mixture to be decolorized contains mono-5-butyl nonylphenol.

9. The method of claims 7 or 8 in which the decolorization reaction takes place at a temperature in the range of 25° to 115° C. and a pressure in the range of atmospheric to 100 psig.

10. A method for decolorzing a mixture of t-butyl nonylphenols containing mono-5-butyl nonylphenol derived by reacting isobutylene with nonylphenol where the nonylphenol is made over an anionic ion-exchange resin catalyst comprising reacting the mixture with trioxane in proportions of 1 to 20 weight percent of the mixture in a homogeneous liquid phase reaction at a temperature in the range of 25° to 115° C. and a pressure in the range of atmospheric to 100 psig.

11. A method for decolorizing a mixture of nonylphenols suitable for use as peroxide inhibitors in polyurethane polyols, the mixture comprising a major portion which is di-t-butyl nonylphenol and a minor portion which is mono-5-butyl nonylphenol, derived from nonylphenol made over an anionic ion-exchange resin catalyst comprising reacting the mixture with 1 to 20 weight percent of trioxane in a liquid phase reaction at a temperature in the range of 25° to 115° C.

* * * * *